United States Patent [19]
Zambrano

[11] Patent Number: 6,019,186
[45] Date of Patent: *Feb. 1, 2000

[54] DISPOSABLE STETHOSCOPE ASSEMBLY

[76] Inventor: Sergio-Sanchez Zambrano, Rte. 5, Box 35A, Cleburne, Tex. 76031

[ * ] Notice: This patent issued on a continued prosecution application filed under 37 CFR 1.53(d), and is subject to the twenty year patent term provisions of 35 U.S.C. 154(a)(2).

[21] Appl. No.: 08/834,438

[22] Filed: Apr. 16, 1997

[51] Int. Cl.⁷ .................................................... A61B 7/02
[52] U.S. Cl. ........................................... 181/131; 181/137
[58] Field of Search .................................. 181/131, 137; 381/67; 128/715

[56] References Cited

U.S. PATENT DOCUMENTS

| | | | |
|---|---|---|---|
| 3,276,536 | 10/1966 | Littmann | 181/137 |
| 3,867,925 | 2/1975 | Ersek . | |
| 4,461,368 | 7/1984 | Plourde . | |
| 4,475,619 | 10/1984 | Packard | 181/137 |
| 4,867,268 | 9/1989 | Ulert . | |
| 5,424,495 | 6/1995 | Wurzburger . | |
| 5,448,025 | 9/1995 | Stark et al. . | |
| 5,466,897 | 11/1995 | Ross et al. . | |

*Primary Examiner*—Khanh Dang
*Attorney, Agent, or Firm*—Felsman Bradley Vaden Gunter & Dillon, LLP; James E. Bradley

[57] ABSTRACT

A thin, disposable shield serves as a sanitary cover as well as a diaphragm for a stethoscope. The shield has a circular line of perforations, resulting in a central disk portion and an outer ring portion. The shield is releasably secured to the rim, preferably by adhesive, to protect a patient from contact with the rim. The shield itself serves as the diaphragm, vibrating with sound transmission. The perforations optionally allow the disk portion to be punched out to provide an unobstructed path for sound transmission of lower frequency. If the forward face of the threaded ring of a conventional stethoscope is not flat, a substitute ring may be secured in place of the conventional ring. The substitute ring has a flat face that is perpendicular to the longitudinal axis. The flat face enhances the ability of the shield to stick to the ring.

17 Claims, 1 Drawing Sheet

DISPOSABLE STETHOSCOPE ASSEMBLY

TECHNICAL FIELD

This invention relates in general to stethoscopes and in particular to a disposable stethoscope bell cover.

BACKGROUND ART

Stethoscopes are used by medical practitioners to listen to the sounds emitted by the internal organs of patients. A stethoscope typically has two cylindrical bells located on opposite sides of its head. One of the bells is smaller than the other and it is used to listen to low frequency sounds. The larger bell is to listen to high frequency sounds. The smaller bell is open-ended while the larger bell is covered by a diaphragm.

It is common for some medical practitioners to use the same stethoscope on every patient without thoroughly cleaning the stethoscope after each use. This practice increases the risk of spreading germs and bacteria from one patient to another.

There are a number of devices shown in patents to prevent spreading of germs with stethoscopes. The devices generally comprise disposable covers which are releasably secured over the diaphragm. Some use adhesive while others use different types of retainers. However, to applicant's knowledge such devices are not commercially available. Furthermore, none of these prior art devices provides a clean surface for the smaller bell, nor are any capable of effectively transmitting both high and low frequency sound emissions.

DISCLOSURE OF INVENTION

A thin, disposable shield is provided as a cover as well as a diaphragm for a stethoscope. The conventional diaphragm is not used. The shield has a circular line of perforations defining a central disk. The shield is releasably secured to the rim, preferably by adhesive, to protect a patient from contact with the rim. The shield itself serves as the diaphragm, vibrating with sound transmission. The perforations optionally allow the disk to be punched out to provide an unobstructed path for sound transmission of lower frequency. The smaller bell need not be used.

The shield may be used on stethoscopes which have threaded rings to hold conventional diaphragms. A substitute ring is secured in place of the conventional ring. The substitute ring has a flat face that is perpendicular to the longitudinal axis. The flat face enhances the ability of the shield to stick to the ring.

BEST MODE FOR CARRYING OUT THE INVENTION

Figure 1:
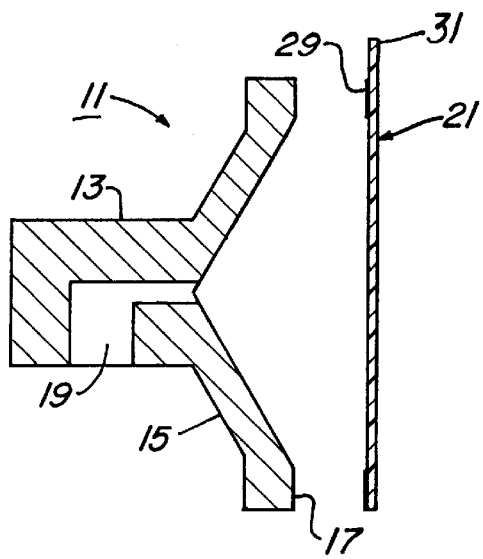
FIG. 1 is a sectional side view of a stethoscope bell and disposable shield constructed in accordance with the invention.

Referring to FIG. 1, head 11 of a stethoscope is shown. Head 11 has a cylindrical body 13 with a longitudinal axis 14, a conical bell 15 with a flat, annular flat surface or rim 17, and a throat or conduit 19 for transmitting sound to the earpieces (not shown) of the stethoscope. Head 11 has only a single bell 15 which is used both for lower and higher frequency sound transmission. Bell 15 is open, having no diaphram.

Figure 2:
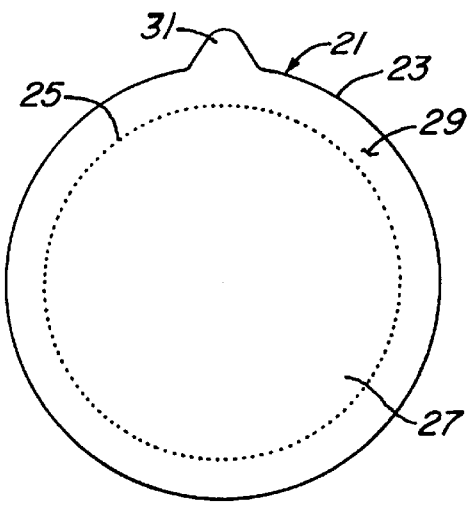
FIG. 2 is a rear view of shield of FIG. 1.

A thin, disposable shield 21 that is circular in shape is adapted to fit over bell 15. As shown in FIGS. 1 and 2, shield 21 comprises a circular member with a central circular line of perforations 25 spaced inward from the periphery and coincident with the longitudinal axis 14. Perforations define a ring portion 23 surrounding a circular disk portion 27. Shield 21 may be made of a paper material and has the same outer diameter as rim 17. An inner side of ring portion 23 is coated with a bonding agent or adhesive 29. Adhesive 29 is preferably a light coating of pressure sensitive adhesive for releasably bonding shield 21 to rim 17. Shield 21 optionally may have a small radial tab 31 located along the circumferential edge of ring 23. The adhesive sides 29 of a plurality of shields 21 may be removably secured to a release means (not shown) such as a paraffincoated roll of paper.

In operation, shield 21 is removed from a release means (not shown) by pulling upward on tab 31, thereby exposing adhesive 29. Shield 21 is placed on head 11 by aligning and pressing ring portion 23 onto rim 17. Adhesive 29 is of sufficient strength to keep shield 21 in place during routine medical examinations. When installed, shield 21 prevents rim 17 from coming into contact with patients. With disk portion 27 in place, shield 21 serves as a diaphragm to allow high frequency sounds to be effectively transmitted and heard by a medical practitioner listening through the stethoscope. The inner side of disk portion 27 is free of contact with any part of bell 15 so as to freely vibrate when shield 21 is placed in contact with a patient. Sound waves transmit directly from shield 21 to throat 19.

Low frequency sounds may be heard by punching out disk portion 27 along perforation line 25, leaving only ring portion 23. Disk 27 may be left in bell 15 or completely removed to provide an unobstructed path for sound transmission. Perforations 25 enable disk 27 to be easily punched out from shield 21. Once disk 27 is removed, a new shield 21 must be installed on rim 17 in order to listen to high frequency sounds. After being used with one patient, shield 21 may be easily removed from rim 17 by pulling tab 31 away from head 11.

Figure 3:
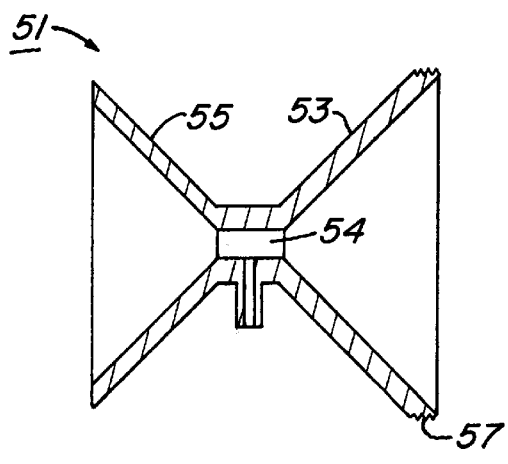
FIG. 3 is an exploded sectional side view of second embodiment of a stethoscope for use with the shield of FIG. 2.

In order to maintain a clean environment with a conventional dual-bell stethoscope, the smaller bell must not be used. Referring to FIG. 3, a conventional stethoscope is shown retrofitted to be used with this invention. Stethoscope head 51 has a longitudinal axis 52, a throat 54, a high frequency bell 53 and a low frequency bell 55. The outer edge 57 of the circular open end of bell 53 is threaded. The conventional diaphragm (not shown) is normally retained by a threaded ring (not shown). The conventional diaphragm and threaded ring are removed. An adapter ring 61 is provided which has a threaded inner diameter 65 for engaging threads 57 and a flat outer face 63. Adapter ring 61 has a central hole equal to the inner diameter of bell 53 at the outer end. Ring 61 is permanently mounted to bell 53 in place of the prior art ring.

Shield 21 (FIG. 2) releasably secures to face 63 of ring 61 in the same manner as it sticks to rim 17 of bell 15 (FIG. 1). Shield 21 transmits sound, serving as a diaphragm in the same manner as described above. Once disk portion 27 is punched out, low frequency sound may be heard through bell 53, unobstructed by disk portion 27. In order to maintain a clean environment, low frequency bell 55 should not be used.

While the invention has been shown in only two of its forms, it should be apparent to those skilled in the art that it is not so limited, but is susceptible to various changes without departing from the scope of the invention.

I claim:

1. A stethoscope, comprising in combination:
   a head with a longitudinal axis and a generally conical portion extending along the axis from a throat to a circular rim;
   a thin, disposable diaphragm;
   a layer of adhesive on one side of the diaphragm which releasably attaches the diaphragm to the rim; and
   wherein sound waves emanating from a patient being examined by use of the stethoscope vibrate the diaphragm, and pass unobstructed from the diaphragm to the throat.

2. The stethoscope according to claim 1 wherein the circular rim comprises a ring which secures by threads to the head, and wherein the ring has a substantially flat face.

3. The stethoscope according to claim 1 wherein the diaphragm has a circular line of perforations defining a central disk portion and an outer ring portion; and wherein
   the perforations optionally allow the disk portion to be punched out.

4. The stethoscope according to claim 1 wherein the disposable diaphragm is made of paper.

5. The stethoscope according to claim 1 wherein the rim is flat.

6. The stethoscope according to claim 1 wherein the stethoscope is free of any structure from the throat to the diaphragm.

7. The stethoscope according to claim 1 wherein a central portion of the diaphragm is located radially inward from a portion of the diaphragm which adheres to the rim, the central portion being free of contact with any structure so as to freely vibrate due to sound waves emanating from a patient.

8. A stethoscope, comprising in combination:
   a generally conical head having a throat one end and a circular rim;
   a thin, disposable diaphragm releasably attached to the rim by an adhesive; and
   wherein the head is free of any structure between the diaphragm and the throat so that sound waves emanating from a patient being examined by use of the stethoscope vibrate the disposable diaphragm and pass unimpeded to the throat.

9. The stethoscope according to claim 8 wherein the circular rim is flat.

10. The stethoscope according to claim 8 wherein the circular rim comprises a ring which secures by threads to the head, and wherein the ring has a substantially flat face.

11. The stethoscope according to claim 8 wherein the diaphragm has a circular line of perforations defining a central disk portion and an outer ring portion; and wherein
    the perforations optionally allow the disk portion to be punched out.

12. The stethoscope according to claim 8 wherein the disposable diaphragm is made of paper.

13. The stethoscope according to claim 8 wherein the rim is flat.

14. The stethoscope according to claim 8 wherein the stethoscope is free of any structure from the throat to the diaphragm.

15. The stethoscope according to claim 8 wherein a central portion of the diaphragm is located radially inward from a portion of the diaphragm which adheres to the rim, the central portion being free of contact with any structure so as to freely vibrate due to sound waves emanating from a patient.

16. A method of using a stethoscope to reduce a chance of spreading germs from one patient to another, the stethoscope having a head with a throat, a conical portion extending from the throat to a circular rim, the method comprising:
    (a) providing a thin, disposable diaphragm with an adhesive layer on one side;
    (b) attaching the disposable diaphragm to the rim by use of the adhesive layer; and
    (c) placing the disposable diaphragm in contact with the patient and listening through the stethoscope, with sound waves from the patient vibrating the disposable diaphragm and passing unimpeded to the throat.

17. The method according to claim 16 further comprising:
    providing the disposable diaphragm with a circular line of perforations defining a central disk portion and an outer ring portion; and wherein
    step (b) comprises attaching the outer ring portion to the rim; and wherein the method further comprises:
        after completing step (c), punching out the central disk portion at the perforations, placing the outer ring portion against a patient, and listening through the stethoscope.

* * * * *